United States Patent
Homent et al.

(10) Patent No.: US 6,540,078 B1
(45) Date of Patent: Apr. 1, 2003

(54) CLOSABLE CONTAINER COMPRISING AT LEAST THREE TRAYS

(76) Inventors: Matthew Homent, 17 Pippin Close, Cambridge, CB4 SUA (GB); John Farboud, 17 Wordsworth Grove, Cambridge, CB3 9HH (GB)

( * ) Notice: Subject to any disclaimer, the term of this patent is extended or adjusted under 35 U.S.C. 154(b) by 0 days.

(21) Appl. No.: 09/508,843

(22) PCT Filed: Sep. 16, 1998

(86) PCT No.: PCT/GB98/02810

§ 371 (c)(1),
(2), (4) Date: May 10, 2001

(87) PCT Pub. No.: WO99/14134

PCT Pub. Date: Mar. 25, 1999

(30) Foreign Application Priority Data

Sep. 16, 1997 (GB) ............................................... 9719552
Nov. 16, 1997 (GB) ............................................... 9724106

(51) Int. Cl.$^7$ ............................................... B65D 51/18
(52) U.S. Cl. ....................................... 206/438; 220/839
(58) Field of Search ........................ 206/369, 370–373, 206/438, 570–572, 745–750; 220/23.6, 23.8, 522, 839; 229/406

(56) References Cited

U.S. PATENT DOCUMENTS

| | | | | |
|---|---|---|---|---|
| 294,938 A | * | 3/1884 | Traver | 206/748 |
| 3,013,656 A | * | 12/1961 | Murphy, Jr. | 206/572 |
| 3,058,579 A | * | 10/1962 | Morin et al. | 206/748 |
| 3,933,296 A | * | 1/1976 | Ruskin et al. | 229/406 |
| 4,336,883 A | * | 6/1982 | Krug et al. | 220/839 |
| 4,501,363 A | * | 2/1985 | Isbey, Jr. | 206/570 |
| 4,928,830 A | * | 5/1990 | Brewer | 206/570 |
| 4,989,733 A | * | 2/1991 | Patry | 206/570 |
| 5,031,768 A | * | 7/1991 | Fischer | 206/370 |
| 5,307,535 A | * | 5/1994 | Reuter et al. | 206/472 |
| 5,323,898 A | * | 6/1994 | Kester | 220/522 |
| 5,346,677 A | * | 9/1994 | Risk | 206/438 |

* cited by examiner

*Primary Examiner*—Jim Foster
(74) *Attorney, Agent, or Firm*—Cowan, Liebowitz & Latman, P.C.; Mark Montague

(57) ABSTRACT

A multipart tray (1) comprises tray elements (2, 3, 4) which can be folded to form a container and in which, when open, the support points for each such tray element are coplanar with the support points of each other tray element. The multipart tray (1) can comprise three tray elements (2, 3, 4) in a linear arrangement. The container can provide a plurality of enclosures arranged to be opened in sequence. The container is intended for use as a sterile field.

21 Claims, 4 Drawing Sheets

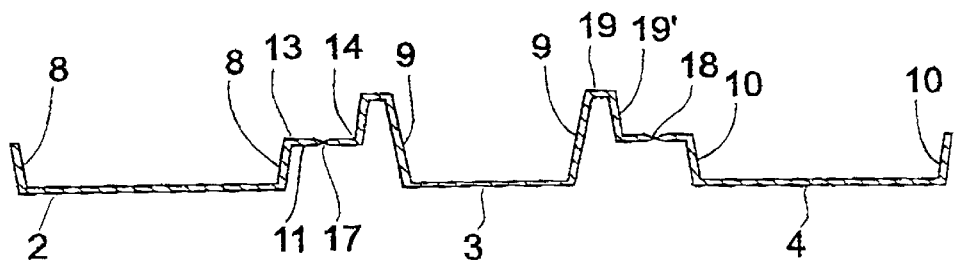
Figure 3
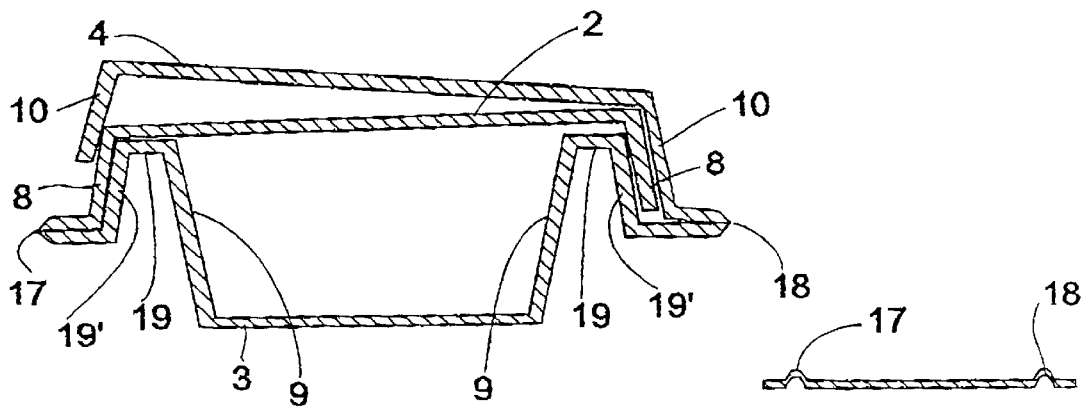
Figure 4
Figure 7
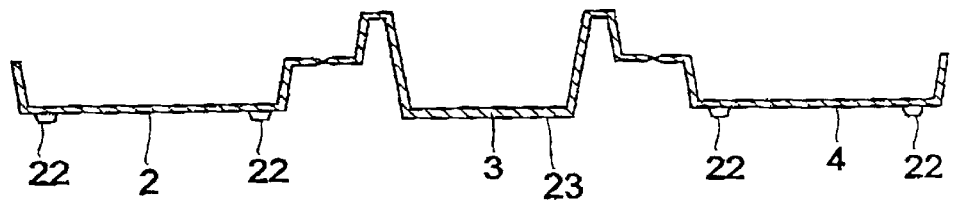
Figure 5
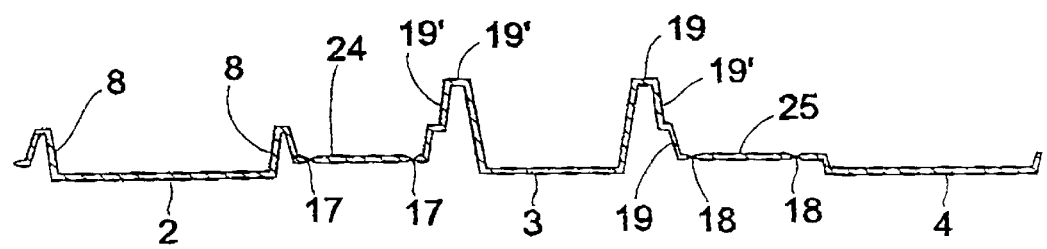
Figure 6

CLOSABLE CONTAINER COMPRISING AT LEAST THREE TRAYS

This invention relates to containers for holding articles, especially medical dressings and utensils, which is adapted when opened to be used also as a sterile working surface for the articles.

When nurses are required to tend a patient, often they will require articles such as dressings and medicaments for the patient. In addition any implements used during treatment must be kept sterile and must not come into contact with sterile surfaces.it is convenient to provide the dressings, medicaments and any implements in a sterile wrapping for use by the nurse, and conventionally such sterile wrappings have been in the form of a paper wrapping around the articles. In use the paper can be unwrapped and laid out on a surface in order to provide a sterile covering for, or a "sterile field" on, the work surface. The articles can be laid out on the paper surface or sterile field for use. There are disadvantages in such a wrapping, such as that the articles are not very secure on the surface and the paper is an extra item that needs to be disposed of. In addition, the paper surface or other sterile field may not lie satisfactorily flat and the user is tempted to smooth the surface by hand. In doing so there is a risk that they do not use gloves and so contaminate the sterile field.

The invention provides a closable container adapted, when opened, to form a multi part tray comprising at least 3 tray elements connected together, characterised in that each such tray element has points of support for its base (in relation to the surface on which the tray is placed) which are substantially co-planar with the points of support of the other such tray elements. In this context points of support for the base may be generally the lower surface of the base or specific protrusions adapted for supporting the base, both as described below.

In a preferred aspect, the invention provides a container which is suitable for use as a clean, preferably sterile, surface on which to work and to use the contents of the container, in particular to provide a sterile field for use with medical dressings and the like.

In a further preferred aspect, the invention provides such a container which is disposable. In particular, following use of medical dressings or the like the user will wish to dispose of the dressings and other items used in the treatment. It is desirable to provide a container for these which can conveniently be disposed of, and which is sufficiently cheap that disposal is commercially sensible. Accordingly the invention further provides disposable such containers.

By disposable in this context is meant an article which is not intended for continued repeated use. In practice it may be adapted for only single use. Accordingly, as hereinafter described it is convenient to make such articles as integral plastic mouldings. In choosing a suitable moulding materials. weights and dimensions, it is an advantage that such articles may be relatively non-durable (whilst being sufficiently strong to maintain integrity of the container in limited use), as distinct from what would be required for repeated use. For example, a lighter article means that less material is used in the article and its disposal is less costly in material terms. For example, articles in accordance with the invention have been made with weights in the range up to 150 gm. preferably up to 100 gm, particularly in the range 50 to 80 gm.

Preferably the container is adapted so that the tray elements form the enclosure of the container. When closed the container can provide one or more enclosures within the container for holding the thing(s) to be contend.

When fully opened the tray can be placed on a flat supporting surface and each of the tray elements will have points of contact with the supporting surface so that that tray element is reasonably secure. When such tray element has supporting contact with the supporting surface it may be used for working on and the risk that the whole tray will be distorted by such working, and accordingly that the contents of the tray may be upset, is reduced.

Preferably the tray elements are connected together by hinges between adjacent tray elements.

The hinge means may be provided along the whole of the length of the adjacent edges of two adjacent tray elements, or along parts of it. For example the hinge means may comprise a section of flexible plastics material linking the two adjacent tray elements together. The section of plastics material may be moulded or scored in a manner to provide a preferential hinge line or more than one preferential hinge line. For example the area of the hinge line may be weakened by scoring; or the adjacent plastics material may be strengthened in some manner, for example by ribbing; or a rib may be provided along the hinge line to encourage bending in the region of that rib. Such hinges may be in the form of living hinges of known type Conveniently the hinge means may also be adapted to ensure that two adjacent tray elements, when folded together, lie substantially over one another and, when opened, have their points of support for their respective bases substantially co-planar. The hinge means may comprise a spacer element to space the hinge line(s) from one or both adjacent tray elements, and/or may have more than one preferential hinge line about which the adjacent tray elements may be folded. For example, the hinge element may conveniently comprise a flexible plastics material section joining the adjacent tray elements and having two substantially parallel hinge lines spaced apart by a spacing element, such that the hinge element is articulated. The hinge element may conveniently have a dog-leg or step in it to assist in alignment of the parts when in the open and closed positions.

Preferably, the hinge element is adapted such that it adopts at least one stable open position such that the support points for the bases of adjacent tray elements are substantially co-planar. This may be achieved by the moulding process, for example, the hinge element may retain a "memory" of the desired open position, or by other means such as, for example, a butterfly type hinge of the type known from, for example, flip top bottle caps.

The tray elements are preferably in the form of a base surrounded by generally upstanding side walls. Usually, the base will be generally flat, but may have moulded components as described below. On the lower surface of the base (the underside of the tray element), there will be provided "base support points". Usually the "base support points" will be the lower (under) surface of the tray element itself. In this case there is less risk that the tray element will itself distort when pressure is applied to the surface. However, they may be provided by, for example, protrusions from the surface which may form feet to support the base of the tray element. This may be desirable where the surface on which the container is likely to be opened is not itself a smooth surface.

Some or all of the tray elements may be provided with further flange sections extending from the surrounding side walls in order to facilitate the formation of a closed container, or adapted to locate adjacent tray elements so that their base support points lie substantially on this same plane. For example, such flanges may be provided on one tray element such that they engage the upstanding side walls on the adjacent tray element, when that element is folded over to cover the first tray element. In one embodiment the flanges are in the form of continuous extension of the existing side walls of the tray element, but are folded outwards and downwards so as to form a skirt encompassing the tops of the side walls of the tray element, the outer surface of the skirt being complementary in profile to the inner surface of the side walls of the adjacent tray element so that, when the adjacent tray element is folded over, it mates onto the skirt section.

The tray elements preferably each have a generally tray shaped form, and may be in the form of plain tray elements comprising only a base and surrounding side walls. Conveniently, they may also have moulded internal components such as moulded sections for holding specific articles to be enclosed within the container. For example there may be recesses shaped to secure bottles or other fluid containers. Alternatively, or in addition, the trays may be provided with inserts which are adapted to secure or hold articles within the container or tray. Conveniently, the tray elements are of broadly rectangular shape, and preferably each of such tray elements is of substantially the same dimensions when viewed in plan.

In one preferred embodiment at least two of the tray elements, for example, the two end tray elements in a linear arrangement, have substantially planar base surfaces so that they can be used as working surfaces in part of a sterile field.

Conveniently, the container will be of a size which is convenient to carry in a single hand without a handle, so that it can be carried by the user while carrying out other activities, and so that it is easy to manipulate.

Suitable planar dimensions for tray elements in container according to the present invention are from 8 cm to 20 cm wide and 15 cm to 30 cm long, preferably 12 cm to 16 cm wide and 20 cm to 25 cm long, for example planar dimensions of about 13 cm by 22 cm have been found to be useful.

Preferably such a container will also be lightweight, so that it is easy to manipulate, in contrast to cases sometimes used for medical implements which are intended to be robust and durable and to provide longterm protection for their contents. Examples of weights of containers which have been made in accordance with the invention are referred to above.

Conveniently one or more tray elements may have a further insert, also of plastics material, adapted to fit closely the interior of the tray element. For example, in some applications it is convenient to have a collector for fluids, for example used washing fluids, and the collector bowl may be in the form of a shallow bowl or tray having a shape which substantially conforms to the shape of the interior of one of the tray elements.

The tray elements may differ in depth, for example, as illustrated in the figures. Preferably at least one tray element (the principal tray element) is internally about 2 cm to 6 cm deep, preferably 3 cm to 5 cm deep, for example a depth of about 4 cm has been found very useful. The other tray elements may conveniently be less deep, for example, a second tray element may be from 1 cm to 3 cm, preferably 1.5 cm to 2.5 cm deep; and a third element just sufficiently deep to prevent articles from sliding from the tray surface, for example, about 1 cm deep.

The tray elements can be linked together in any convenient arrangement such that they can be folded up to form the container and, when open, form a substantially planar multi part tray. Conveniently they are in a linear arrangement, with one tray element at each end, and tray elements located in a linear chain between the end elements. Preferably there are three way elements, and preferably in a linear arrangement as shown in the figures.

For example, according to one construction, the tray comprises three or more rectangular tray elements. The tray elements are connected together in a linear manner, so that a first tray element forms one end of a line of tray elements; that tray element is connected to a second tray element along their common edge through hinge means; the second tray element is connected to a third tray element along the edge opposite to the first tray element, along the common edge between the second and third tray elements, also by hinge means.

When in the form of a container, the central tray element is intended to hold the contents of the container. One end tray element is folded over by the hinge means to form a cover over the central tray element, and the second end tray element is then folded also over the central tray element, and secures the first end tray element between itself and the central tray element.

As referred to above the container may have more than one enclosed volume for holding contained things. For example it may have one enclosure, such as that described above, formed between the central tray element and the first end tray element, and a second enclosure between the first end tray element and the second end tray element. The latter may be formed by having a recess in the floor of the first tray element so that, when the second tray element is folded over it, the recess in the floor of the first tray element, and the floor of the second tray element enclose or partially enclose a volume, for use as an enclosure. Alternatively, or in addition, the second tray element may be spaced away from the first tray element in the folded position, so that an enclosure is formned between the two elements. It will be apparent that other configurations of container can be adapted to similar effect The container may be sealed by, for example, applying sealing tape about the openable edges of the container, or may be placed in a wrapper, such as a plastic bag, and sealed and/or shrink wrapped within such bag. Previously paper wrappers have been used for dressing packages and the container according to the invention could be wrapped or sealed in paper. Generally, such containers are intended for use in a sterile environment, and will be sterilised by conventional means, for example, after closing and usually after packaging in wrapping. A container according to the invention may conveniently contain items such as scissors, swabs, latex gloves, stitches, a disposable bag, syringes, needles, dressings, fluid containers, and other surgical sundries, such as surgical blades.

In use, the user will break open the packaging around the container, and open out each of the tray elements so that it lies open on the intended working surface, with the base of each tray element supported by the working surface. The user can then use each tray element for different parts of the user's activities. For example, one tray element may be identified as for "clean" materials, and a second tray element identified for "soiled" materials, so that the user can clearly identify which articles have already been used.

Conveniently, the contents can be arranged in the container in an order which encourages their correct use. Preferably a container having more than one enclosure is used, and when opened these enclosures will be opened in the correct sequence. For example, in one embodiment a cleaning tissue is provided so that the user cleans their hands before handling the remaining contents of the container. This tissue can be provided as the first accessible item in the first opened enclosure, such as the space between the first and second end elements described in one embodiment above. Similar items such as instructions for use, waste disposal bags and the like can be provided in this enclosure. Only after these contents have been removed is it then convenient for the user to open the second enclosure and obtain access to the next items to be used, for example sterile dressings and the like.

Containers according to the present invention are preferably made from plastics material, for example, high impact polystyrene. They may be made by any moulding means. Conveniently, however, they are made by vacuum or pressed moulding, and can be made of such design that such moulding can be relatively easily carried out. The container of the invention may also be made by injection moulding. Preferably, such containers are of an integral design in which each of the tray elements, and the hinge means are in one part (although the tray elements may have additional inserts for holding articles within the tray) Preferably, therefore, the container is made from sheet plastics material, for example relatively thin, preferably relatively uniform thickness sheet plastics material. Conveniently the thickness of the moulded plastics material in the moulded article is relatively uniform. For example, it may be made from sheet plastics material of 400 gauge to 800 gauge, preferably 600.

The invention is now further described by way of example only by reference to the accompanying drawings.

FIG. 3 is cross-section taken across the line AA in FIG. 2.

FIG. 4 is a cross-section, along the line AA in FIG. 2, of the container in a partially closed position.

FIGS. 5 and 6 are cross-sections of alternative embodiments of the container.

FIG. 7 shows a cross-sectional detail of one hinge embodiment.

The figures are not necessarily to scale.

Figure 2:
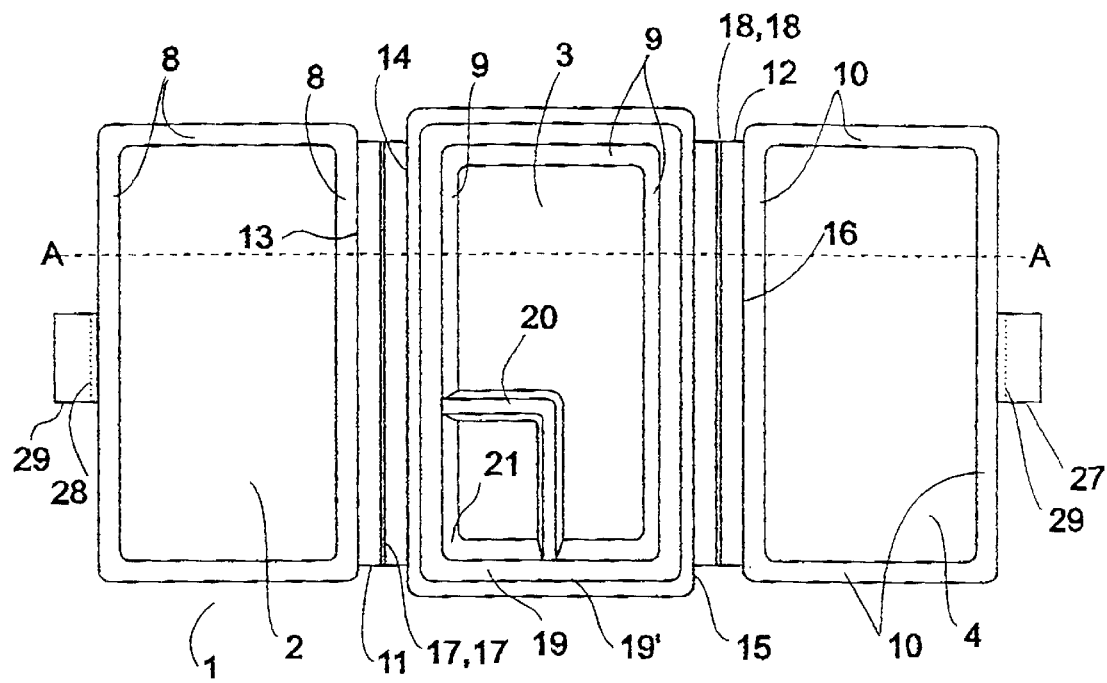
FIG. 2 is a plan view of the same container.
Figure 1:
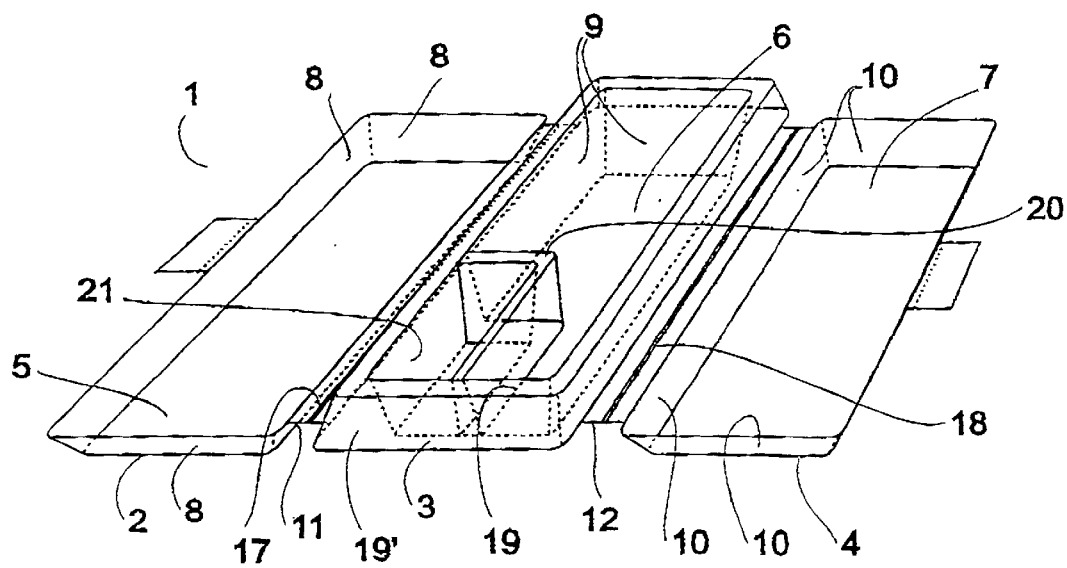
FIG. 1 is a perspective view of the container in accordance with the invention.

FIG. 1 shows a multi part tray 1, comprising three tray elements 2, 3, 4. Each tray element comprises a base respectively 5, 6, 7 surrounded by upstanding walls 8, 9, 10 (not all of which are specifically identified). Each of the tray elements 2, 3, 4 is of generally rectangular shape. Adjoining tray elements are integrally connected by a hinge element 11, 12. The hinge element shown in FIGS. 1 and 2 is in the form of a plastics material strip running substantially the fill length of the adjacent edges 13, 14 and 15, 16 of the adjacent tray elements 2, 3, 4 The plastic strips 11, 12 have a relatively flexible pair of hinge lines together marked as 17, 18 about which the hinge can be flexed.

The central tray element 3 has a further flange comprising components 19, 19' extending outwardly and downwardly from the tops of the side walls 9, and forming a peripheral skirt surrounding and depending from the tops of the side walls 9. The hinge elements 11 and 12 are connected to the lower edges 14 and 15 of the depending skirt 19'.

In addition, central tray element 3 is provided with a further moulded enclosure 20. In practice, this may conveniently be in the form of a circular recess, rather than as shown as a rectangular recess, having a volume of about 60 ml. The recess may be used to secure and store conventional pot shaped containers, and conveniently the angle 21 is retained as an angle so that a user can place a finger between the secured pot and the tray interior, in order to remove the pot from its position.

The tray elements 2 and 4 are also shown with tabs, 26 and 27, which may be used to facilitate opening of the container, so that the user avoids touching the body of the tray at all. The tabs are provided with perforations, 28 and 29, forming a weakened line. The tabs can be broken or torn off at the tear line after the container has been opened so as to leave the remaining elements of the container uncontaminated.

FIG. 4 shows the container of FIG. 1 in a partially closed position. Tray element 2 has been folded over the central tray element 3 about hinge lines 17. Central tray element has flange extensions 19, 19' element 19' forming a peripheral skirt depending from the tops of the side walls 9 The outer surface of the skirt 19' engages the inner surface of side walls 8 of tray element 2, forming a mating engagement which permits the container to be closed. The shape of skirt 19 is designed to be complementary to the inner surface of the side walls 8 of tray element 2.

The second end tray element, 4, is then folded over, about the hinge lines 18 so as to engage the outer surface of tray element 2. The inner surfaces of side walls 10 are designed to have a complementary surface to the outer surface of side walls 8.

FIG. 5 shows an alternative embodiment of the container in FIG. 1, in which the lowest surface of tray elements 2 and 4 are provided with base support points 22. It will be observed that the lower surface of base support points 22 and the lower surface 23 of the base 6 of tray element 3 are substantially co-planar.

FIG. 6 shows a further alternative construction. In this construction, adjacent tray elements 2 and 3, and 3 and 4 are spaced apart by spacer elements 24, 25 forming part of hinge elements 11 and 12 respectively. Each hinge element is provided with two hinge lines 17, 18 about which tray elements 2 and 4 can be rotated and folded over tray element 3. The spacer elements 24, 25 provide suitable positioning to ensure that, when tray element 2 is folded over tray element 3, the internal surfaces of side walls 8 of tray element 2 engage, in a mating relationship, the external surfaces of flange elements 19, forming the peripheral skirt around the tops of side walls 9 of tray element 3. In addition, the articulated hinge arrangement of hinge elements 11, 12 permits tray elements 2, 4 to be positioned so that their lower surfaces are substantially co-planar with the lower surface of tray element 3.

FIG. 7 shows an alternative hinge construction in which the hinge lines 17, 18 are in the form of ribs.

Figure 8:
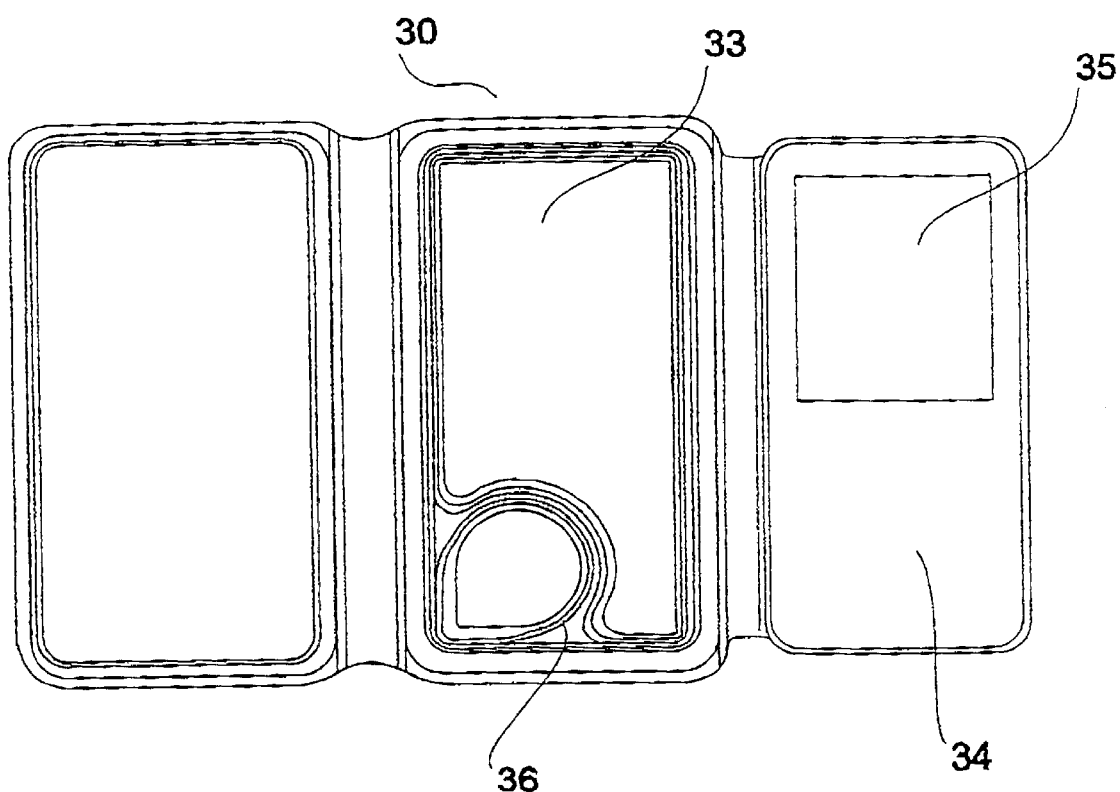
FIG. 8 is a line drawing in cross-section of a further embodiment of the invention.
Figure 9:
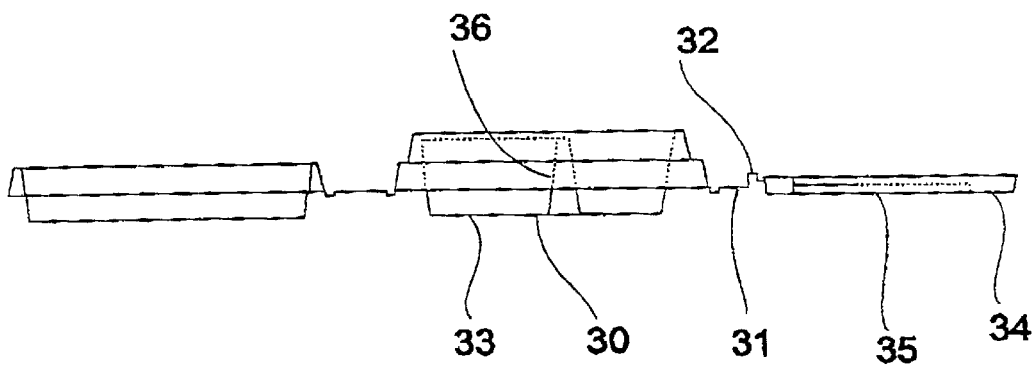
FIG. 9 is a plan view of the same embodiment.

FIGS. 8 and 9 show a further embodiment of the same type of container.

In this container (30) one of the hinge elements (31) has a step or dog leg (32) to assist in aligning the tray elements (33, 34) in both the open and closed positions. In addition tray element 34 has a rectangular recess 35, into which contents such as the cleaning tissue and waste bag can be located. In addition a moulded receptacle (36) integral with central tray element (33) suitable for securing fluid flasks or bottles is shown.

Figure 10:
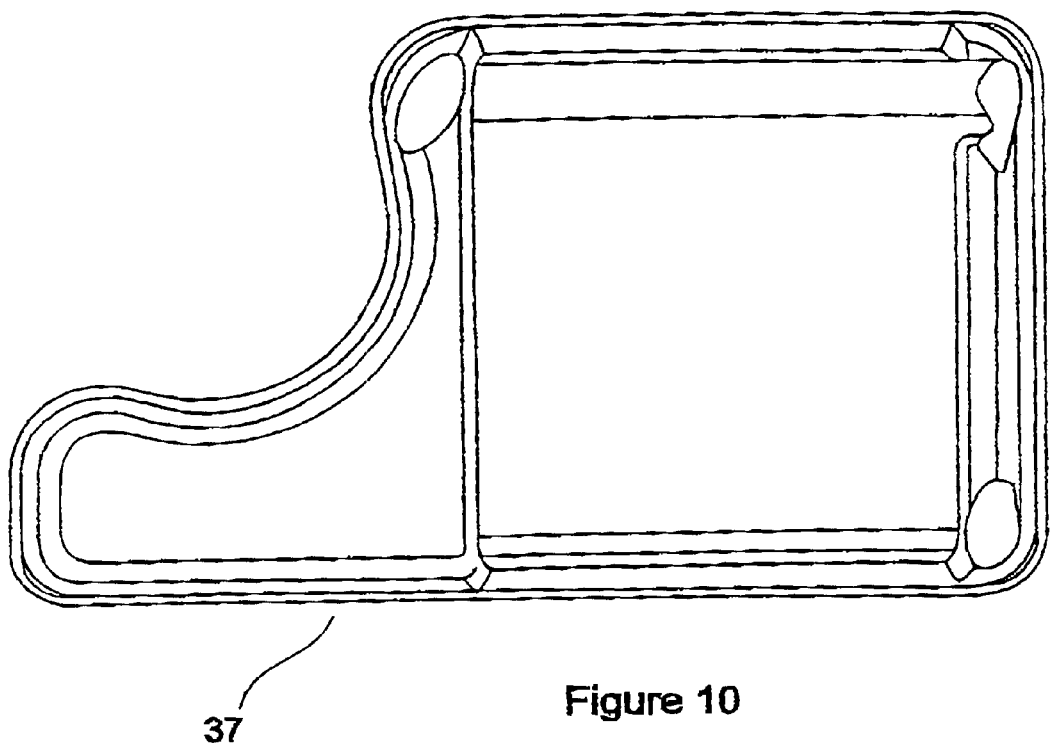
FIG. 10 is a view in elevation of a collector tray for use in the embodiment of FIGS. 8 and 9.
Figure 11:
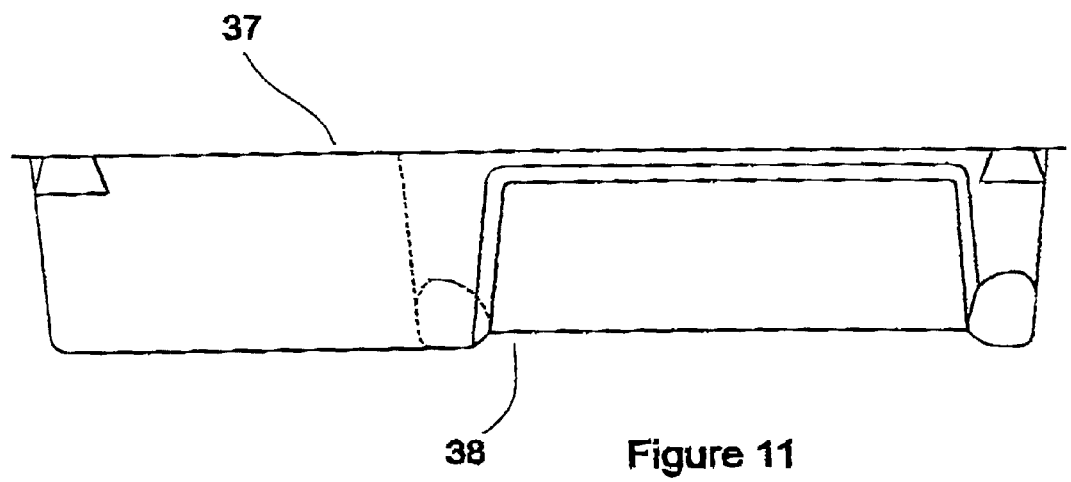
FIG. 11 is a plan view of the same collector.

FIG. 10 shows the edge of a collector tray (37) in elevation. FIG. 11 shows the same collector in plan. The collector tray is moulded in a shape which conforms with a substantial part of the interior of central tray element 33, fitting around the outside of the integrally moulded recess (36), and fitting closely within the interior of the remainder of the central tray element. The collector itself has a moulded recess (38) on its underside. When the collector (37) is placed in the central tray element (33), the recess forms a cavity into which further contents may be located. In particular this can be used for placing a part of a pair of surgical gloves (not shown) used in the course of the procedures for which the container is used. The surgical gloves are withdrawn at an appropriate stage in the procedure, which facilitates removal of the collector.

What is claimed is:

1. A medical container system comprising:

a first tray element having base support points;

a second tray element having base support points and connected to the first tray element by a first hinge;

a third tray element having base support points and connected to the second tray element by a second hinge; and one or more medical articles, wherein the first tray element, the third tray element, or both the first and third tray elements can be folded about the respective first and second hinge means to substantially cover the second tray element to form a confined space to contain the medical articles, wherein the first and third tray elements are rotated along the first and second hinges, respectively, to open the container system to form a multi-part tray system in which the base support points of each tray element are substantially coplanar, and wherein the multi-part tray system forms a sterile field.

2. The medical container system of claim 1, wherein the medical articles are selected from the group consisting of medical dressings, medical utensils, and medical instruments.

3. The medical container system of claim 1 which is disposable.

4. The medical container system of claim 1, wherein, when the container system is closed, at least one tray element is adapted to hold the contents of the container system and at least one other tray element is adapted to close the container system.

5. The medical container system of claim 4 which has at least two enclosed spaces adapted to receive articles to be held in the container system, the second enclosed space being formed between a third tray element and at least one other tray element.

6. The medical container system of claim 1, wherein each hinge comprises a hinge element comprising a flexible plastic material component lying between and connected to the adjacent tray elements.

7. The medical container system of claim 6, wherein the hinge elements have at least one relatively flexible hinge line such that the connected tray elements can be folded together about the hinge line in such a manner that one tray element lies substantially over the other tray element.

8. The medical container system of claim 7, wherein at least one of the hinge elements has at least two hinge lines separated by a spacer element to form an articulated hinge element.

9. The medical container system of claim 6, wherein the hinge elements are adapted to adopt a relatively stable position in the open configuration of the container.

10. The medical container system of claim 1, wherein the tray elements are arranged linearly.

11. The medical container system of claim 10, wherein the first and third tray elements in the linear arrangement have tabs adapted to facilitate opening.

12. The medical container system of claim 1, wherein each tray element has a base surrounded by upstanding sidewalls.

13. The medical container system of claim 1, wherein there is a principal tray element adapted to hold the contents of the container, at least a second tray element is hingedly connected to the principal tray element along one common edge, at least a third tray element is hingedly connected to the principal tray element along a different common edge, in which the second tray element is folded over the principal tray element along the hinge between the two elements so as to substantially close over the principal tray element, and the third tray element is folded over the second tray element in a nesting manner.

14. The medical container system of claim 13, wherein there is a second enclosed space formed between the second and third tray elements.

15. The medical container system of claim 1, wherein each tray element has been sterilized.

16. The medical container system of claim 1, which also comprises a collector tray having a shape substantially conforming to the interior of the second tray element.

17. The medical container system of claim 1, wherein the medical articles are medical dressings.

18. The medical container system of claim 1, wherein there are at least two enclosed spaces which are arranged so that, during opening of the container they are opened in sequence, in which the contents of the container which are intended to be used first are placed in the first accessible enclosed space and those intended to be used thereafter, in a subsequently opened enclosed space.

19. The medical container system of claim 1 which is sealed by a sealing tape around its open edges or enclosed in a sealed sterilizable plastic enclosure.

20. A sterile working surface for use when treating patients comprising a closable medical container system of claim 1 adapted, when opened, to form a multi-part tray having at least three tray elements connected together, characterized in that each tray element has base support points which are substantially co-planar with the base support points of the other such tray elements.

21. In a method of treating a patient wherein one or more medical articles are used by a doctor during the course of treatment, the improvement wherein a medical container system of claim 1 is provided, said container system is opened to provide medical articles in a sterile field, and the doctor takes said medical articles from said sterile field.

* * * * *